US010806621B2

(12) United States Patent
Quist (10) Patent No.: US 10,806,621 B2
(45) Date of Patent: Oct. 20, 2020

(54) CLAVICLE FRACTURE INFANT BRACE

(71) Applicant: SPROSSENTECH, LLC, Lehi, UT (US)

(72) Inventor: Kirsten Quist, Lehi, UT (US)

(73) Assignee: SPROSSENTECH, LLC, Lehi, UT (US)

(*) Notice: Subject to any disclaimer, the term of this patent is extended or adjusted under 35 U.S.C. 154(b) by 531 days.

(21) Appl. No.: 15/482,504

(22) Filed: Apr. 7, 2017

(65) Prior Publication Data

US 2017/0290696 A1 Oct. 12, 2017

Related U.S. Application Data

(60) Provisional application No. 62/321,680, filed on Apr. 12, 2016.

(51) Int. Cl.
| | |
|---|---|
| *A61F 5/058* | (2006.01) |
| *A61F 5/37* | (2006.01) |
| *A61F 5/01* | (2006.01) |
| *A61F 5/04* | (2006.01) |
| *A61F 5/05* | (2006.01) |
| *A41B 13/06* | (2006.01) |

(52) U.S. Cl.
CPC ........ *A61F 5/05808* (2013.01); *A61F 5/0102* (2013.01); *A61F 5/013* (2013.01); *A61F 5/0118* (2013.01); *A61F 5/04* (2013.01); *A61F 5/05* (2013.01); *A61F 5/058* (2013.01); *A61F 5/37* (2013.01); *A61F 5/3723* (2013.01); *A41B 13/06* (2013.01)

(58) Field of Classification Search
CPC ........ A61F 5/0109; A61F 5/0118; A61F 5/04; A61F 5/05; A61F 5/05858; A61F 5/37; A61F 5/3715; A61F 5/3723; A61F 5/3738; A61F 13/08; A61F 13/085; A41B 13/06

USPC ...... 602/4, 20, 22, 30, 62, 63; 128/869, 870, 128/872–876, 878; 5/482, 494; 2/69, 2/69.5
See application file for complete search history.

(56) References Cited

U.S. PATENT DOCUMENTS

| | | | | |
|---|---|---|---|---|
| 3,515,131 | A | * | 6/1970 | Stevens ................ A61F 5/3738 602/20 |
| 3,970,316 | A | * | 7/1976 | Westmoreland, Jr. .................... A63B 69/0059 473/212 |
| 5,772,617 | A | | 6/1998 | Lay |
| 6,393,612 | B1 | * | 5/2002 | Thach ................. A41B 13/065 2/69.5 |

(Continued)

FOREIGN PATENT DOCUMENTS

WO 2017180516 10/2017

OTHER PUBLICATIONS

International Search Report and Written Opinion for application No. PCT/US17/026813 dated Jun. 27, 2017.

*Primary Examiner* — Keri J Nelson
(74) *Attorney, Agent, or Firm* — Bateman IP (57) ABSTRACT

The present disclosure describes an infant brace for treating an infant with a fractured clavicle. The infant brace includes a torso portion for receiving the donning infant's torso, and an arm portion for receiving the donning infant's arm on the side coinciding with the fractured clavicle. The infant brace is formed from an elastic netting material. The infant brace provides effective immobilization of the infant's affected upper arm while minimizing risks of over-heating or causing pressure sores.

19 Claims, 5 Drawing Sheets

(56) References Cited

U.S. PATENT DOCUMENTS

| | | | |
|---|---|---|---|
| 7,073,204 B1* | 7/2006 | Boyles | A41D 13/1236 2/114 |
| 9,060,549 B2* | 6/2015 | Buckson | A61F 5/3723 |
| 2009/0282599 A1* | 11/2009 | Comerford | A41B 13/06 2/69.5 |
| 2010/0064411 A1 | 3/2010 | Price | |
| 2013/0139290 A1* | 6/2013 | Barski | A41B 13/06 2/69.5 |
| 2013/0237893 A1 | 9/2013 | Knox | |
| 2016/0081844 A1* | 3/2016 | Wagner | A61F 5/3738 602/4 |
| 2016/0157642 A1* | 6/2016 | Xiong | A47G 9/083 2/80 |

* cited by examiner

CLAVICLE FRACTURE INFANT BRACE

CROSS-REFERENCE TO RELATED APPLICATIONS

This application claims priority to and the benefit of U.S. Provisional Patent Application Ser. No. 62/321,680, filed on Apr. 12, 2016 and titled "INFANT BRACE," the disclosure of which is incorporated herein by this reference in its entirety.

BACKGROUND

Clavicle fractures occur in approximately 3% of infants born in the United States, most commonly after prolonged or otherwise difficult vaginal births. Because of the fracture, the infant experiences pain when the shoulder is moved and/or when the infant is lifted, in particular when the infant is lifted from under the arms. Generally, there is no treatment other than advising parents/caretakers to lift the child gently to prevent discomfort. In addition, the infant's arm on the affected side is usually immobilized to minimize upper arm movement while the fracture heals. Typically, immobilization is accomplished by putting the infant in a long-sleeve shirt, positioning the affected arm over the infant's abdomen, and simply pinning the sleeve in place.

Although preventing some movement, the common approach of putting an infant in a long-sleeved shirt and pinning the shirt to hold the affected arm in position still allows substantial upper arm movement. For example, an infant can typically still substantially move the shoulder via elevation and depression (i.e., shrugging the shoulder) and via retraction and protraction (i.e., rolling the shoulder). Further, the infant will often still be capable of some amount of shoulder rotation, shoulder flexion/extension, shoulder abduction, or other shoulder movements. Such movements may slow healing of the clavicle.

In addition, the infant will be able to move the arm within the pinned sleeve to the degree that the sleeve allows. While a tighter fitting sleeve can minimize such movement intra-sleeve motion, clothes with such tighter fitting sleeves likely require more manipulation of the arm just to get the arm into the sleeve.

Conventional immobilization braces may be used to treat infant clavicle fractures. However, these typically include fastening hardware made from metal or hard plastic and/or require a relatively large surface area of hook and loop fastener material. These components are irritating to an infant's sensitive skin and can potentially create pressure sores as a result of the infant lying too long in one position. As compared to older children and adults, infants move considerably less and must lie down for a greater proportion of each day, exacerbating the risk of getting such pressure sores.

Further, as compared to adults, infants have limited ability to regulate body temperature. Conventional brace and bandage materials often fail to provide much breathability. When used on older children and adults, such materials may cause greater sweating or slight discomfort. However, when used on infants, the risk of causing overheating is a valid concern.

BRIEF SUMMARY

The present disclosure describes infant braces which may be utilized to immobilize movement of an infant's upper arm in order to promote healing of a fractured clavicle and/or minimize pain associated with the fractured clavicle. In some embodiments, an infant brace includes a torso portion and an arm portion joined to the torso portion. The torso portion is configured in size and shape to receive a torso of the donning infant, and the arm portion is configured in size and shape to receive an arm of the infant on a side of the infant corresponding to the fractured clavicle. The torso portion and arm portion have a cylindrical/tubular formation with openings on each opposing end.

In some embodiments, the torso portion and arm portion are joined by a first seam which extends along a coinciding length of the torso portion and arm portion. In some embodiments, the first seam extends across substantially the entire length of the arm portion and/or the torso portion. In some embodiments, the torso portion and the arm portion have lengths that are substantially the same. For example, the torso portion and the arm portion may have lengths of about 10 cm to about 20 cm.

In some embodiments, the infant brace is formed from an elastic netting material. The infant brace may be formed from a material including one or more of nylon, polyester, rayon, spandex, rubber, or a combination thereof. In some embodiments, the infant brace is formed from a material having effective elasticity, such as an elasticity that allows the circumference of the torso portion and/or arm portion to vary by a factor of about 1.5 to 4 between a non-stretched configuration and a stretched configuration.

In some embodiments, the infant brace is formed from a breathable material. For example, the infant brace may be formed from a material having a thread count (when in a non-stretched configuration) of about 30 to 70. The material may have a thread count in a stretched configuration (e.g., when donned on the infant) of about 12 to 28. In some embodiments, the infant brace is formed from a material such that when the infant brace is donned, a surface area of the material is about 25% or more open space.

In some embodiments, the infant brace beneficially omits fasteners which could cause and/or aggravate pressure sores, or which could otherwise irritate a donning infant's relatively sensitive skin.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which.

DETAILED DESCRIPTION

The present disclosure is directed to infant braces which may be utilized to immobilize movement of an infant's upper arm in order to promote healing of a fractured clavicle and/or minimize pain associated with the fractured clavicle. Embodiments described herein may be positioned on an infant with a fractured clavicle to minimize or prevent movement that may disrupt or prolong healing of the fractured clavicle. At least some embodiments described herein may provide effective immobilization and promotion of clavicle healing while minimizing risks of overheating the donning infant, causing pressure sores, falling out of proper position, or insufficiently immobilizing the targeted arm.

Figure 1:
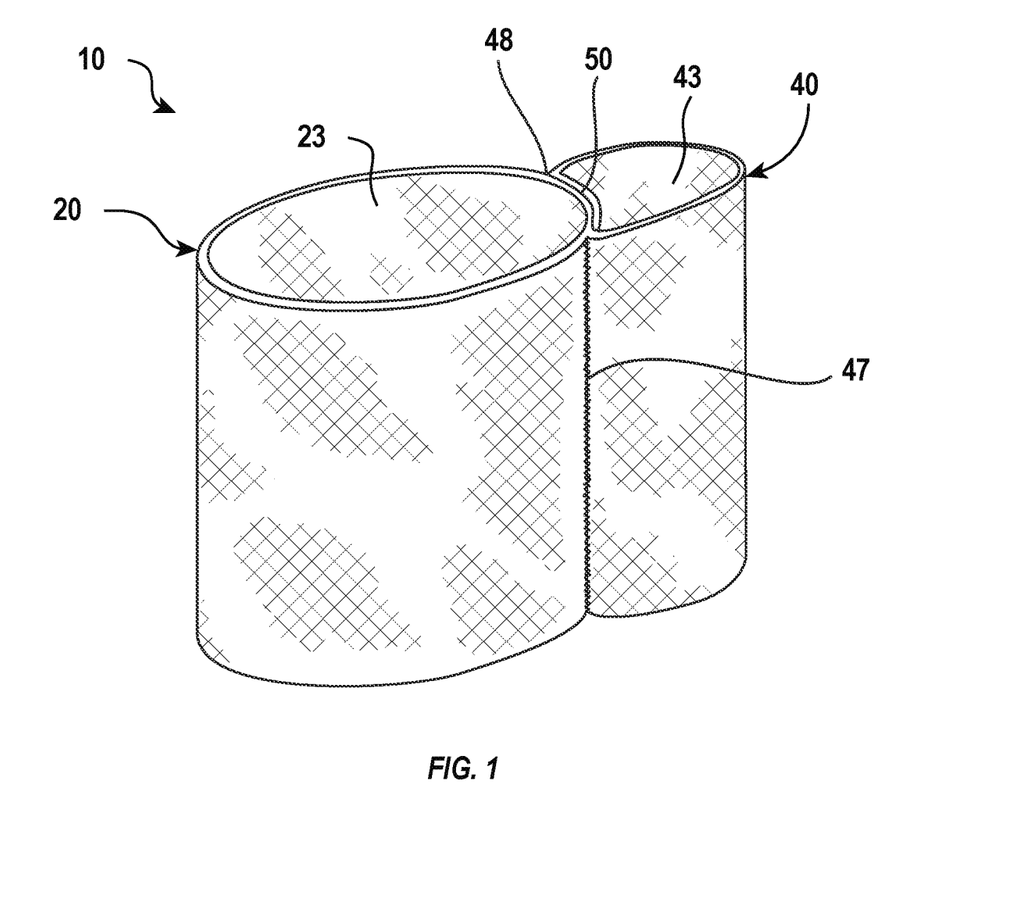
FIG. 1 illustrates a perspective view of an infant brace which may be utilized to immobilize an infant's upper arm to promote healing of a fractured clavicle.

FIG. 1 illustrates a perspective view of an exemplary infant brace 10. The illustrated infant brace 10 includes a torso portion 20 and an arm portion 40, each of which has a generally cylindrical shape. The torso portion 20 has an open first end 23 and an open second end (not visible in the view shown in FIG. 1) opposite the open first end 23. The torso portion 20 defines a space configured in size and shape to receive an infant's torso. Similarly, the arm portion 40 has an open first end 43 and an open second end (not visible in FIG. 1) opposite the open first end 43. The arm portion 40 defines a space configured in size and shape to receive an infant's arm.

The torso portion 20 has a circumference sized to receive an infant's torso, while the arm portion 40 has a circumference sized to receive an infant's arm. In preferred embodiments, the torso portion 20 and arm portion 40 are substantially connected along the entirety of their lengths, as shown. In other embodiments, the torso portion 20 and/or the arm portion 40 may include one or more sections of length not connected to the opposite portion.

In preferred embodiments, the length of the torso portion 20 and arm portion 40 are substantially the same, as shown. In alternative embodiments, the torso portion 20 and arm portion 40 may have different lengths. It will be understood that as the length of the torso portion 20 and arm portion 40 are increased, the mobility of the infant's arm decreases. In some embodiments, the torso portion 20 and/or arm portion 40 have a length of about 5 cm to about 25 cm, or about 10 cm to 20 cm. The length of the torso portion 20 and/or arm portion 40 may be varied according to the size of the infant to be fitted with the infant brace 10 and/or the desired level of mobility of the infant's upper arm.

The infant brace 10 may be constructed of any suitable material. In some embodiments, the infant brace 10 is constructed of a soft material that provides a suitable level of elastic stretch, such as a woven material including one or more of cotton, synthetic fabrics (e.g., nylon, polyester, rayon, spandex (i.e., polyester-polyurethane copolymer)), elastic materials (e.g., rubber), or blends or combinations thereof. Additionally, soft materials are more preferred, as infants often have relatively sensitive skin as compared to children and adults.

In presently preferred embodiments, the infant brace 10 includes or is formed of an elastic netting material, which may also be commonly referred to as elastic net bandage, elastic net dressing, or elastic retention netting. Such elastic netting is often available in a tubular form having a set circumference, which can then be cut by length for particular application needs. Exemplary elastic net dressings utilized in the infant braces described herein may be formed from one or more of rayon, polyester, spandex, nylon, or combinations or blends thereof. For example, effective results have been found using elastic net dressings formed from a rayon and polyester blend, and have been found using elastic net dressings formed from a spandex and polyester blend. One example of a suitable elastic netting material is the "Elastic Net Sleeve" product sold under the trade name Curad® as of April 2017.

In preferred embodiments, the infant brace 10 is formed using a breathable material having an open weave. Such materials may beneficially provide an infant brace with effective breathability relative to conventional elastic bandages (which are typically made from cotton, polyester, and elastic yarns). Effective breathability prevents or minimizes the risk of overheating the infant, as infants are not able to regulate body temperature as well as children and adults. This becomes particularly important in warmer climates and/or during warmer seasons of the year, where the additional thermal burden of the brace materials cannot simply be offset by removing other layers of the infant's clothes.

As used herein, a "breathable" material is a material made using thin thread and/or a low density knit/weave. Typically, such breathable materials are at least somewhat translucent as a result of the low-density knit/weave and or thin thread weight used in the material. For example, when used to form an infant brace as described herein, the infants arm and torso (or the clothes the infant is wearing) will be partially visible through the overlying infant brace. In one example, when the material is in a stretched configuration while donned on an infant, the surface area of the weave will be about 25% or more open space (e.g., between threads), or more preferably about 50% or more open space (e.g., up to about 70%, 80%, 90%, or 95% open space). In contrast, an unbreathable material is one that is relatively more restrictive to the free flow of gases, such as the material construction used in a conventional elastic bandage (e.g., those sold under the trade name ACE™).

Some embodiments may include a material with sufficient elasticity to help in placing the brace on an infant, but not so much elasticity that it allows the infant substantial movement within the brace once the brace has been properly positioned. For example, the infant brace 10 may have a doffed configuration where the circumferences of the torso portion 20 and arm portion 40 are non-stretched and relatively small and a donned configuration where the circumferences of the torso portion 20 and arm portion 40 are stretched to a relatively larger size. In some embodiments, the circumferential ratio between donned and doffed configurations of the torso portion 20 and/or arm portion 40 is about 1.5 to 4, or about 2 to 3, or about 2.5. For example, in a non-stretched/doffed configuration, the torso portion 20 may have a circumference of about 10 to 15 cm, which may stretch when donned on an infant to a circumference of about 28 to 36 cm.

In some embodiments, the material utilized to form the infant brace (such as an elastic netting material) is configured to provide relatively greater elasticity in the lateral or radial direction than in the longitudinal direction. For example, an infant brace may be configured such that the circumferential size of the torso portion and arm portion vary by a factor of 1.5 to 4, or about 2 to 3, or about 2.5 between a non-stretched configuration and a stretched configuration, but the length of the brace remains substantially the same between the non-stretched and stretched configurations, or varies by a factor less than that of the lateral/radial elasticity.

In some embodiments, the infant brace 10 will include a material having a thread count that provides effective breathability. For example, materials having a thread count (per square inch; i.e., 2.54 cm by 2.54 cm) in an non-stretched/doffed configuration of about 30 to 70, or about 40 to 60, or about 45 to 55, have shown effective breathability when utilized in an infant brace as described herein. Such materials, when in a stretched/donned configuration, may have a thread count of about 12 to 28, or about 16 to 24, or about 18 to 22. As used herein, "thread count" may be determined using industry standards of the United States National Textile Association (NTA) as in place as of April of 2017 (e.g., multiple-ply yarns count as one thread).

In some embodiments, such as in a kit embodiment which includes multiple infant braces, a single size of the infant brace may be provided that is configured in size and shape to be suitable for most infants. In other embodiments, infant braces may be provided in a plurality of standard sizes. In some embodiments, an infant brace may be custom sized to fit a particular infant. In some embodiments, a pack/kit of infant braces 10 is provided in a set of standard sizes. For example, two or more of a small, medium, and large size may be provided to accommodate the infant as the infant grows.

The average infant in the United States has a chest circumference of about 30-33 cm (12-13 inches), and thus a standard size of the circumference of the torso portion 20 (e.g., when in a stretched/donned configuration) may be about 28 cm to about 35 cm, or about 30 cm to about 33 cm. Some embodiments may be sized a little larger to accommodate for positioning the brace over clothes. For example, the torso portion may be sized to have a circumference of about 33 cm to about 38 cm, or about 36 cm (e.g., when in a stretched/donned configuration).

The average infant in the United States has a middle upper arm circumference of about 7-14 cm (about 4 inches), and thus a standard size of the circumference of the arm portion (e.g., when in a stretched/donned configuration) may be about 5 cm to about 16 cm, or about 7 cm to about 14 cm. In some embodiments, an additional 0.5 to 2 cm may be added to the circumference in order to accommodate clothing worn by the infant underneath the brace 10. The ratio of the circumference of the torso portion 20 to the arm portion 40 may therefore be about 3 to about 5.

The infant brace 10 may be constructed in several different ways. By way of illustration and not of limitation, some examples of construction will be provided herein. One with skill in the art will appreciate that other methods for constructing the infant brace 10 are possible.

Figure 2:
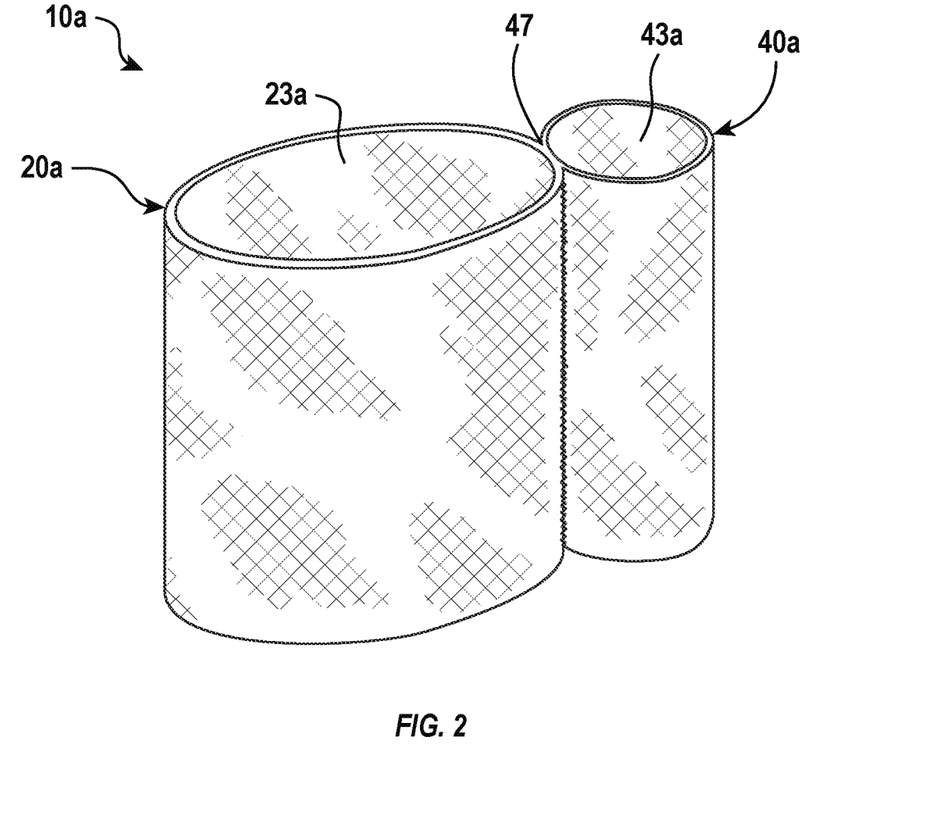
FIG. 2 illustrates another embodiment of an infant brace having a single-seam construction.

FIG. 2 illustrates an infant brace 10a, formed from one exemplary method. According to this method, a seam 47a is formed into a single tubular piece of material, the seam 47a thereby defining and separating the torso portion 20a and arm portion 40a, with respective openings 23a and 43a. The seam 47a may be formed by sewing, stitching, using an adhesive, or combinations thereof.

In an alternative embodiment, the torso portion 20a may be formed by sewing two ends of a length of material together (the length of the material being the desired circumference of the torso portion, plus any seam allowance). Then the arm portion 40a may be formed in a similar manner, with a shorter length of material (the length of the material being the desired circumference of the arm portion, plus any seam allowance). The torso portion 20a and arm portion 40a may then be attached along their lengths, joining them at a seam 47a.

Referring back to FIG. 1, the illustrated infant brace 10 may be constructed by initially forming a first seam 47. The torso portion 20 and arm portion 40 may be two separate pieces joined by the first seam 47, or each may be part of a singular tubular piece of material, with the first seam 47 separating and defining the separate portions. After the first seam 47 has been formed, a portion of the arm portion 40 may be folded over a corresponding portion of the torso portion 20, and a second seam 48 may be formed. An overlapping portion 50 (or partition or divider) is thereby formed between the first seam 47 and the second seam 48.

Embodiments having an overlapping portion 50 have shown to provide effective immobilization of a donning infant's arm. As opposed to the more limited connectivity of single-seam embodiments, in some circumstances an embodiment having an overlapping portion 50 has a greater structural ability to resist an infant's upper arm movements. For example, where a single seam may function as a fulcrum upon which the arm portion 40 may partially pivot or bend relative to the torso portion 20, an embodiment having an overlapping portion 50 is better able to stabilize the arm portion 40 relative to the torso portion 20. The effective stability provided by the overlapping portion 50 may better prevent shoulder flexion/extension movements and external and internal shoulder rotation movements, for example.

In some embodiments, the overlapping portion 50 is sized so as to coincide with about 1% to 15% of the circumference of the torso portion 20, or about 2% to 10% of the circumference of the torso portion 20. In some embodiments, the overlapping portion 50 is sized so as to coincide with about 10% to 30% of the circumference of the arm portion 40, or about 15% to 25% of the circumference of the arm portion 40. An infant brace 10 having an overlapping portion 50 within the foregoing size ranges has been shown to provide effective arm immobilization when donned by an infant.

Figure 3:
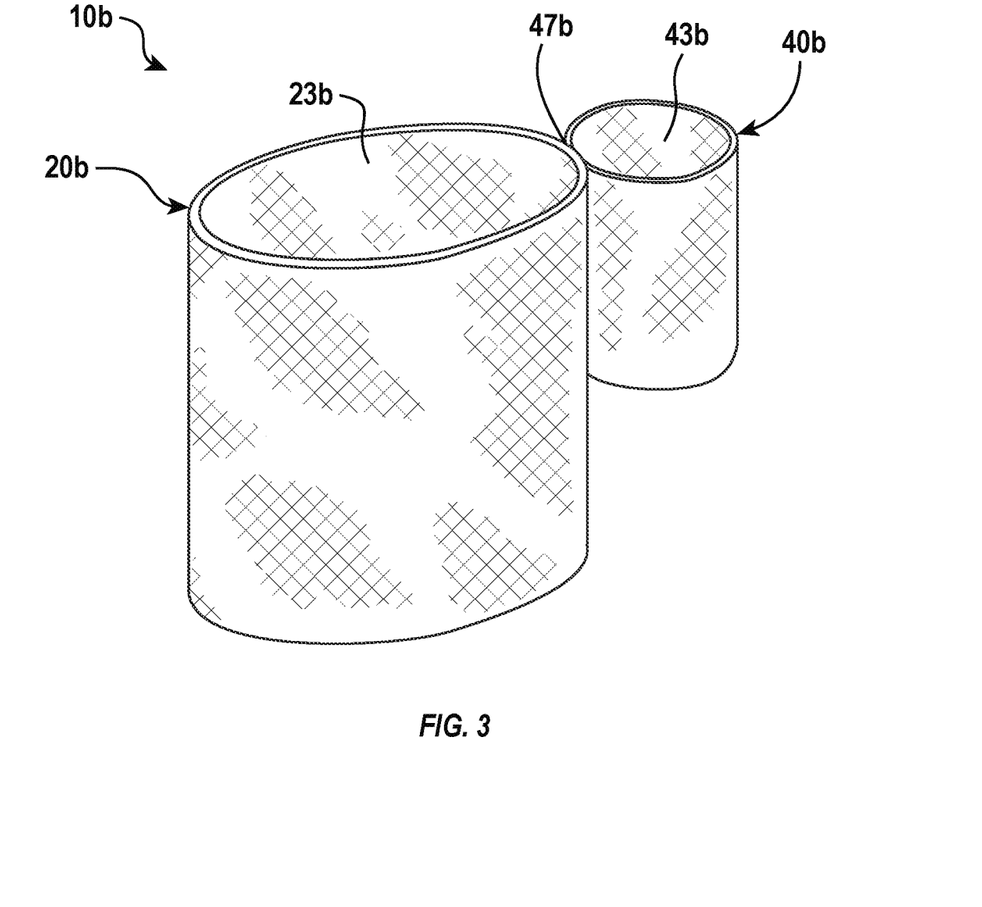
FIG. 3 illustrates another embodiment of an infant brace with an arm portion and torso portion of dissimilar lengths.

FIG. 3 illustrates another embodiment of an infant brace 10b which has a longer length in the torso portion 20b, and a shorter length in the arm portion 40b. In some configurations, such as that shown in FIG. 1, the arm portion 40 and the torso portion 20 may have equally or approximately equal lengths. However, it is also possible to construct a brace with different lengths for the torso portion and arm portion, such as an infant brace having a relatively longer arm portion, or an infant brace having a relatively longer torso portion, as shown in FIG. 3.

The embodiment shown in FIG. 3 may be utilized, for example, where it is desirable or acceptable for the infant to flex/extend the elbow. The arm portion 40b may have a length that extends across most of the donning infant's upper arm, but does not extend in the inferior direction far enough to cover the infant's elbow. Although an embodiment such as the one shown in FIG. 3 allows lower arm movement, the arm portion 40b still maintains the donning infant's upper arm securely against the torso, preventing or minimizing upper arm movements that may be painful and/or which prolong healing time of the clavicle.

An embodiment such as shown in FIG. 3 may be formed after the torso portion 20b and arm portion 40b, with respective openings 23b and 43b have been formed and/or defined by seam 47b, such as by cutting an inferior section of the arm portion 40b to be shorter than the torso portion 20b. Alternatively, the torso portion 20b and the arm portion 40b may be separately formed and sized prior to being attached at the seam 47b.

Figure 4:
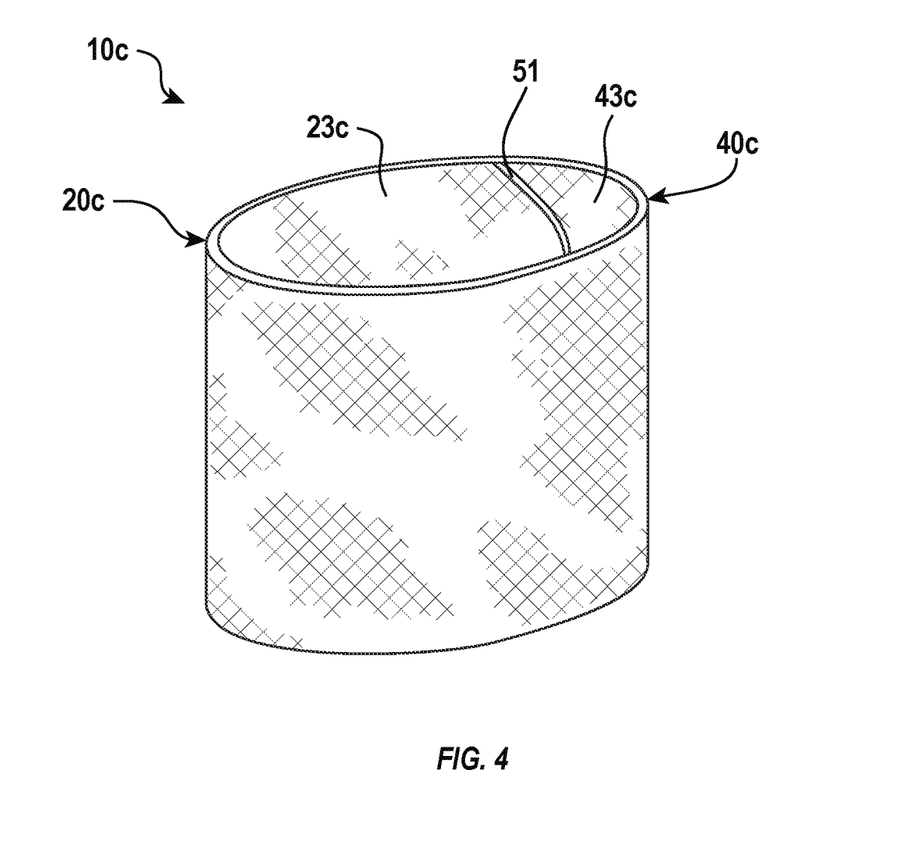
FIG. 4 illustrates another embodiment of an infant brace including a divider for defining and separating a torso portion and arm portion.

FIG. 4 illustrates another embodiment of an infant brace 10c. The infant brace 10c may be formed by providing a length and width of material providing the desired circumference of the infant brace, including the torso portion 20c and the arm portion 40c (plus any desired seam allowance). If not already provided in a tubular form, the ends of the linear section of material may be connected (e.g., by sewing, using an adhesive, and/or other suitable attachment method) to form a tubular member. A piece of material acting as a partition or divider 51 may then be positioned to define the torso portion 20c with an open first end 23c for receiving an infant's torso, and an arm portion 40c with an open first end 43c for receiving an infant's arm.

In use, the infant brace 10 may be donned by positioning it on an infant inferiorly and moving it superiorly. For example, the donning infant's feet may be first placed into the first end 23 of the torso portion 20, and the infant brace moved superiorly to the waist of the infant. Then the hand of the infant (e.g., the hand on the same lateral side as the fractured clavicle) may be placed into the first end 43 of the arm portion 40, and the infant brace moved superiorly until the torso portion 20 extends around the upper torso of the infant and the arm portion 40 extends around the upper arm of the infant.

Figure 5:
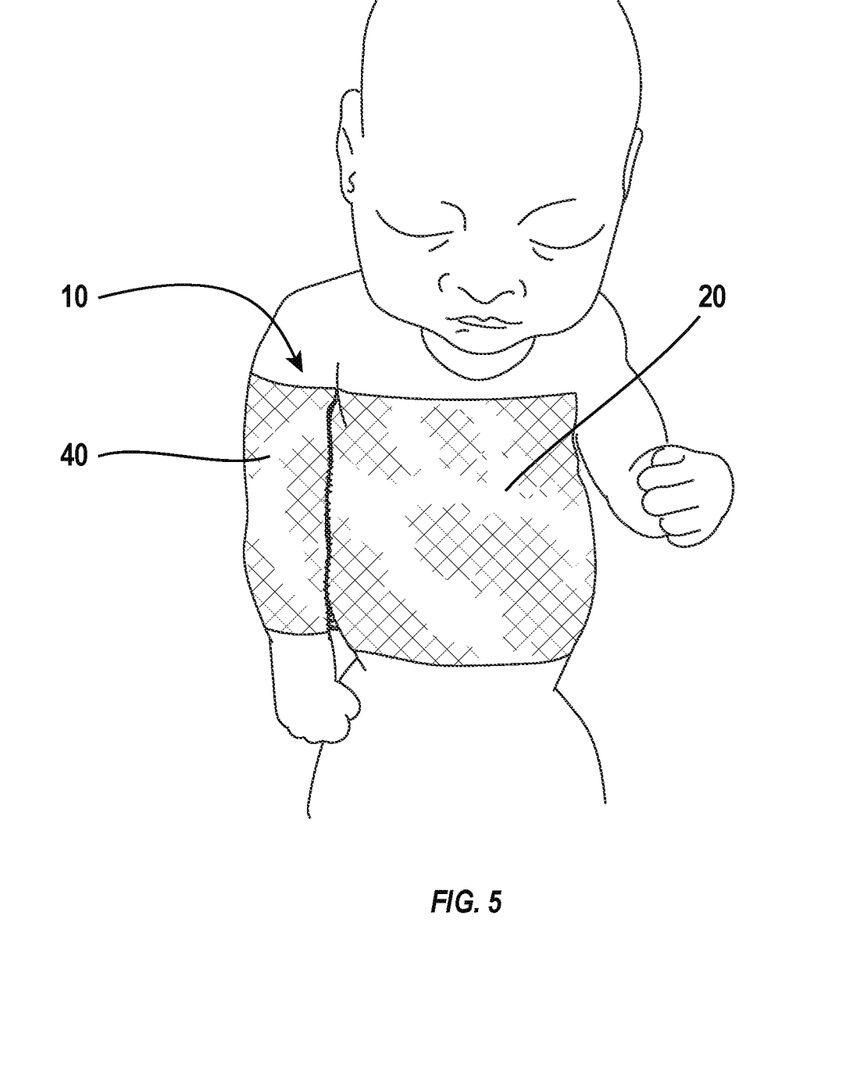
FIG. 5 illustrates the infant brace of FIG. 1 donned on an infant.

FIG. 5 illustrates an infant wearing the exemplary infant brace 10. As shown, the arm portion 40 extends around the upper arm of the infant on the side where the infant has suffered a fractured clavicle. The torso portion 20 extends around the torso of the infant. In the preferred position, as illustrated, the infant's upper arm is immobilized relative to the torso portion 40. In addition, the infant's hand on the affected side is free, allowing the infant to move his/her fingers and wrist. The ability to freely move the fingers and wrist is beneficial, as such movements are developmentally important for infants within the affected age group.

As shown in FIG. 5, the torso portion 20 of the infant brace 10 may have a length such that when the brace is donned, it spans from a position near the infant's armpits to a position near the infant's waist. Other embodiments may have shorter lengths. For example, a length as small as about 2 cm may provide sufficient structure to allow the infant brace to be properly positioned and to provide desired levels of arm immobilization. However, more preferred embodiments are configured with longer lengths such as shown in FIG. 5. For example, the torso portion 20 may have a length of about 10 cm to 25 cm, or about 15 cm to 20 cm, or may be sized according to a particular infant to generally extend from near the armpits to near the waist. Infant braces having lengths such as the foregoing may better engage and hold position when positioned on an infant. For example, an infant brace having such a length may better resist rolling at the edges and sliding out of desired position.

In the illustrated embodiment, the arm portion 40 is substantially the same length as the torso portion 20. Although alternative embodiments may utilize an arm portion with a length that is different compared to the length of the corresponding torso portion (see FIG. 3, for example), presently preferred embodiments include an arm portion 40 with a length approximately the same as that of the torso portion 20. In some circumstances, for example, it may be beneficial to immobilize the infant's lower arm in addition to the infant's upper arm. Limiting the infant's lower arm movement may prevent or reduce the amount of incidental upper arm motion caused by lower arm movement. An arm portion that extends to cover the infant's lower arm therefore prevents or minimizes unwanted upper arm disturbance incidentally caused by excess motive freedom in the lower arm.

The illustrated infant brace 10 is also configured to maintain the infant's arm in a "straight" position with the elbow in extension and the associated arm positioned along the infant's side. In contrast, the conventional position associated with standard braces positions the elbow in partial flexion with the lower arm positioned over the abdomen. The straight-arm position provided by the illustrated infant brace 10 can better immobilize the upper arm and effectively prevent or minimize unwanted upper arm movement. For example, in the straight-arm position with the elbow in full or nearly full extension, the infant is less able and/or less likely to use his/her elbow as a lever point for arm movements that affect the upper arm. In a further example, with the elbow in extension and held to the side, the infant is less able to engage the elbow against his/her side to gain enough traction to rotate the shoulder (e.g., medially or laterally).

At least some of the infant brace embodiments described herein do not include separate fasteners and may be utilized without requiring fasteners for proper placement. Conventional braces often utilize clips, clasps, snap buttons, and the like. Such fasteners typically include metal and/or hard plastic components, which can be irritating to an infant's relatively sensitive skin. In addition, because an infant cannot move as much as an older child or adult, and must lie down for longer periods of time, the infant is particularly susceptible to pressure sores caused by such fasteners. Some conventional braces and bandages utilize hook and loop fasteners. Such material can irritate an infant's skin. Further, the inherent thickness and density of the material reduces the overall breathability of the brace or bandage.

In contrast, exemplary infant braces described herein omit such fasteners and thereby lower or eliminate the risk of brace-caused pressure sores. In addition, the exemplary infant braces described herein omit the relatively thick and dense hook and loop fastener materials and instead maintain effective breathability across substantially all sections of the brace.

Infant braces described herein may allow a donning infant to restrain movement of the upper arm to allow the clavicle to heal properly. At least some embodiments may also allow the donning infant to have moderate use of the hand and fingers on the lateral side of the fractured clavicle. Use of the hands and fingers on the lateral side of the fractured clavicle has not shown to negatively impact healing of the clavicle. Developing infants benefit from the movement of their hands and fingers in exploring their environment. Infant brace embodiments described herein may therefore increase an infant's ability to move their hands and fingers to explore and continue to develop while also beneficially limiting movement of the upper arm which could negatively impact healing of the fractured clavicle.

In addition, infants with a fractured clavicle may experience increased pain when lifted under their arms. With an infant brace as described herein in place on an infant's upper torso and upper arm, it is difficult to lift the infant under his/her arms, as there is generally little to no space under the arm when the infant brace in properly donned. Thus, an infant brace may remind and/or force a caregiver to lift the infant more delicately, which can decrease the pain the infant experiences associated with being lifted under the arms.

The infant brace embodiments illustrated herein show a single arm portion attached to the torso portion. Alternative embodiments may include an arm portion on each side to form two arm portions. It will be understood that the principles described in relation to the single arm portion embodiments may be utilized to form a second arm portion. Infant brace embodiments having two arm portions may be utilized to provide immobilization of both an infant's arms in circumstances where such immobilization is warranted. For example, an infant may be positioned in such a brace to prevent the infant from grasping at and/or pulling oxygen tubing, cannulas, or other medical equipment, or to prevent the infant from touching and aggravating injured areas.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be substituted for or combined with elements described in relation to any other embodiment depicted and/or described herein. For example, any of materials, material properties, or size descriptions described in relation to the embodiment of FIG. 1 may be utilized with any of the alternative embodiments illustrated or described herein.

The invention claimed is:

1. An infant brace for treating a fractured clavicle of a donning infant, the infant brace comprising:
   a torso portion configured in size and shape to receive a torso of the donning infant, the torso portion having a tubular formation with openings on each end of the torso portion;
   an arm portion configured in size and shape to receive an arm of the donning infant on a side of the infant corresponding to the fractured clavicle, the arm portion having a tubular formation with openings on each end of the arm portion,
   wherein the arm portion is joined to the torso portion along a first seam with the arm portion being disposed outside of the torso portion, and wherein lengths of the torso portion and the arm portion between their openings are oriented so as to be substantially parallel to one another; and wherein the infant brace omits fasteners.

2. The infant brace of claim 1, wherein the first seam extends across substantially the entire length of the arm portion.

3. The infant brace of claim 1, wherein the arm portion and the torso portion have lengths that are substantially the same.

4. The infant brace of claim 1, wherein the torso portion and the arm portion have lengths of about 10 cm to about 20 cm.

5. The infant brace of claim 4, wherein the torso portion has a circumference between 28 and 35 cm in a stretched/donned configuration.

6. The infant brace of claim 1, wherein the infant brace is formed of an elastic netting material.

7. The infant brace of claim 6, wherein the infant brace is formed of one or more of nylon, polyester, rayon, spandex, rubber, or a combination thereof.

8. The infant brace of claim 1, wherein the infant brace has elasticity such that a circumference of the torso portion varies by a factor of about 1.5 to 4 between a non-stretched configuration and a stretched configuration.

9. The infant brace of claim 1, wherein the infant brace is formed from a breathable material having a thread count when in a non-stretched configuration of about 30 to 70.

10. The infant brace of claim 1, wherein a ratio of a circumference of the torso portion to a circumference of the arm portion is about 3 to 5.

11. The infant brace of claim 1, further comprising a second seam joining the torso portion to the arm portion, and further comprising an overlapping portion formed between the first and second seams, the overlapping portion forming part of the circumference of the torso portion and part of the circumference of the arm portion.

12. The infant brace of claim 11, wherein the overlapping portion coincides with about 1% to about 15% of the circumference of the torso portion.

13. The infant brace of claim 1, wherein the infant brace is formed of a material such that when the infant brace is donned, a surface area of the material is about 25% or more open space.

14. The infant brace of claim 1, wherein the arm portion is formed by a continuous piece of fabric extending from the point or points at which the arm portion extends from the torso portion and wherein the torso portion is formed from a continuous piece of fabric from the point or points at which the arm portion extends from the torso portion.

15. The infant brace of claim 1, wherein the torso portion has a length of between 10 and 20 cm and a stretch circumference of between 28 and 35 cm.

16. An infant brace for treating a fractured clavicle of a donning infant, the infant brace comprising:
   a torso portion configured in size and shape to receive a torso of the donning infant, the torso portion having a continuous, tubular formation with openings on each end of the torso portion;
   an arm portion joined to the torso portion, the arm portion configured in size and shape to receive an arm of the donning infant on a side of the infant corresponding to the fractured clavicle, the arm portion having a continuous, tubular formation with openings on each end of the arm portion, the arm portion extending along an exterior of the torso portion so as to be generally parallel with the torso portion as the arm portion and the torso portion extend between their respective openings;
   wherein the torso portion and arm portion are formed of an elastic netting material, and
   wherein the infant brace has elasticity such that a circumference of the torso portion and a circumference of the arm portion vary by a factor of about 1.5 to 4 between a non-stretched configuration and a stretched configuration; and
   and wherein the infant brace omits fasteners.

17. The infant brace of claim 16, wherein the infant brace is formed from a breathable material having a thread count when in a non-stretched configuration of about 30 to 70.

18. The infant brace of claim 16, wherein the infant brace is formed of a material such that when the infant brace is donned, a surface area of the material is about 25% or more open space.

19. The infant brace of claim 16, wherein the arm portion is between 10 and 20 cm in length and wherein the torso portion can stretch to have a circumference of between 28 and 35 cm.

* * * * *